(12) United States Patent
Rammeloo et al.

(10) Patent No.: US 8,772,512 B2
(45) Date of Patent: Jul. 8, 2014

(54) CRYSTALLISATION PROCESS FOR 1-(β-D-GLUCOPYRANOSYL)-4-METHYL-3-[5-(4-FLUOROPHENYL)-2-THIENYLMETHYL] BENZENE

(75) Inventors: Thomas Joachim Landewald Rammeloo, Vosselaar (BE); Ruben De Keyser, Retie (BE); Gustaaf Jozef Petrus Schildermans, Balen (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/382,658

(22) PCT Filed: Jul. 8, 2010

(86) PCT No.: PCT/EP2010/059817
§ 371 (c)(1),
(2), (4) Date: Jan. 6, 2012

(87) PCT Pub. No.: WO2011/003976
PCT Pub. Date: Jan. 13, 2011

(65) Prior Publication Data
US 2012/0108824 A1      May 3, 2012

(30) Foreign Application Priority Data
Jul. 10, 2009   (EP) .................................... 09165125

(51) Int. Cl.
  *C07D 409/10*    (2006.01)
  *C07D 309/10*    (2006.01)
(52) U.S. Cl.
  CPC .................................. *C07D 309/10* (2013.01)
  USPC ........................................................ 549/60
(58) Field of Classification Search
  CPC .................................................. C07D 309/10
  USPC ........................................................ 549/60
  See application file for complete search history.

(56) References Cited

U.S. PATENT DOCUMENTS

| | | | |
|---|---|---|---|
| 2,799,241 A | 7/1949 | Wurster | |
| 4,160,861 A | 7/1979 | Cole et al. | |
| 4,584,369 A | 4/1986 | Klein et al. | |
| 5,149,838 A | 9/1992 | Humphrey et al. | |
| 5,292,461 A | 3/1994 | Juch et al. | |
| 5,401,435 A | 3/1995 | Burzio et al. | |
| 5,424,406 A | 6/1995 | Tsujihara et al. | |
| 5,610,294 A | 3/1997 | Lam et al. | |
| 5,731,292 A | 3/1998 | Tsujihara et al. | |
| 5,767,094 A | 6/1998 | Tsujihara et al. | |
| 5,780,483 A | 7/1998 | Widdowson et al. | |
| 5,830,873 A | 11/1998 | Tsujihara et al. | |
| 5,861,385 A | 1/1999 | Angerbauer et al. | |
| 5,945,533 A | 8/1999 | Kometani et al. | |
| 6,048,842 A | 4/2000 | Tsujihara et al. | |
| 6,069,238 A | 5/2000 | Hitchcock et al. | |
| 6,153,632 A | 11/2000 | Rieveley | |
| 6,277,833 B1 | 8/2001 | Angerbauer et al. | |
| 6,297,363 B1 | 10/2001 | Kubo et al. | |
| 6,414,126 B1 | 7/2002 | Ellsworth et al. | |
| 6,420,513 B2 | 7/2002 | Minami | |
| 6,448,415 B1 | 9/2002 | Lee et al. | |
| 6,475,521 B1 | 11/2002 | Timmins et al. | |
| 6,515,117 B2 | 2/2003 | Ellsworth et al. | |
| 6,562,791 B1 | 5/2003 | Maurya et al. | |
| 6,617,313 B1 | 9/2003 | Maurya et al. | |
| 6,627,611 B2 | 9/2003 | Tomiyama et al. | |
| 6,800,761 B1 | 10/2004 | Franc et al. | |
| 7,008,959 B2 * | 3/2006 | Franc et al. | .................... 514/381 |
| 7,045,665 B2 | 5/2006 | Fujikura et al. | |
| 7,074,826 B2 | 7/2006 | Wechter et al. | |
| 7,084,123 B2 | 8/2006 | Fujikura et al. | |
| 7,202,350 B2 | 4/2007 | Imamura et al. | |
| 7,271,153 B2 | 9/2007 | Nishimura et al. | |
| 7,288,528 B2 | 10/2007 | Frick et al. | |
| 7,294,618 B2 | 11/2007 | Fushimi et al. | |
| 7,375,213 B2 | 5/2008 | Deshpande et al. | |
| 7,417,032 B2 | 8/2008 | Eckhardt et al. | |
| 7,511,022 B2 | 3/2009 | Beavers et al. | |
| 7,566,699 B2 | 7/2009 | Fushimi et al. | |
| 7,576,064 B2 | 8/2009 | Kikuchi et al. | |
| 7,666,845 B2 | 2/2010 | Cook et al. | |
| 7,932,379 B2 | 4/2011 | Deshpande et al. | |
| 7,943,582 B2 | 5/2011 | Nomura et al. | |
| 7,943,788 B2 | 5/2011 | Nomura et al. | |
| 2001/0041674 A1 | 11/2001 | Tomiyama et al. | |
| 2002/0032164 A1 | 3/2002 | Dale et al. | |
| 2002/0052326 A1 | 5/2002 | Washburn | |

(Continued)

FOREIGN PATENT DOCUMENTS

| | | |
|---|---|---|
| CA | 2494177 A1 | 2/2004 |
| EP | 0355750 A1 | 2/1990 |

(Continued)

OTHER PUBLICATIONS

International Search Report relating to International Patent Application No. PCT/EP2010/059817. Date of Mailing of International Search Report: Aug. 5, 2010.
Written Opinion of International Searching Authority relating to International Patent Application No. PCT/EP2010/059817. Date of Mailing of Written Opinion: Aug. 5, 2010.
Adachi et al., "Jan. 1095, a Renal Na+Glucose Transporter Inhibitor, Improves Hyperglycemia in Streptozotocin-Induced Diabetic Rats.", Metabolism, Aug. 2000, pp. 990-995, vol. 49(8).
Ahmad et al., "Synthesis and Structure Determination of Some Oxadiazole-2-Thione and Triazole-3-Thione Galactosides.", Nucleosides, Nucleotides & Nucleic Acids, 2001, pp. 1671-1682, vol. 20(9).

(Continued)

*Primary Examiner* — Noble Jarrell
*Assistant Examiner* — John S Kenyon

(57) ABSTRACT

The present invention relates to a crystallization procedure to obtain 1-(β-D-glucopyranosyl)-4-methyl-3-[5-(4-fluorophenyl)-2-thienylmethyl] benzene hemihydrate crystals having a narrow particle size distribution and improved flowability, bulk and tap density properties.

15 Claims, 4 Drawing Sheets

(56) References Cited

U.S. PATENT DOCUMENTS

| | | |
|---|---|---|
| 2002/0111315 A1 | 8/2002 | Washburn et al. |
| 2003/0024914 A1 | 2/2003 | Aleshin |
| 2003/0064935 A1 | 4/2003 | Gougoutas |
| 2003/0087843 A1 | 5/2003 | Washburn |
| 2003/0114390 A1 | 6/2003 | Washburn et al. |
| 2003/0191121 A1 | 10/2003 | Miller et al. |
| 2004/0053855 A1 | 3/2004 | Fujikura et al. |
| 2004/0063646 A1 | 4/2004 | Fujikura et al. |
| 2004/0110936 A1 | 6/2004 | Ohsumi et al. |
| 2004/0116357 A1 | 6/2004 | Fushimi et al. |
| 2004/0132669 A1 | 7/2004 | Nishimura et al. |
| 2004/0138143 A1 | 7/2004 | Glombik et al. |
| 2004/0259819 A1 | 12/2004 | Frick et al. |
| 2005/0014704 A1 | 1/2005 | Frick et al. |
| 2005/0032711 A1 | 2/2005 | Patel et al. |
| 2005/0032712 A1 | 2/2005 | Urbanski |
| 2005/0037980 A1 | 2/2005 | Rybczynski et al. |
| 2005/0037981 A1 | 2/2005 | Beavers et al. |
| 2005/0049203 A1 | 3/2005 | Nishimura et al. |
| 2005/0124555 A1 | 6/2005 | Tomiyama et al. |
| 2005/0124556 A1 | 6/2005 | Burton |
| 2005/0209166 A1 | 9/2005 | Eckhardt et al. |
| 2005/0233988 A1 | 10/2005 | Nomura et al. |
| 2005/0256317 A1 | 11/2005 | Sato et al. |
| 2006/0009400 A1 | 1/2006 | Eckhardt et al. |
| 2006/0035841 A1 | 2/2006 | Eckhardt et al. |
| 2006/0122126 A1 | 6/2006 | Imamura et al. |
| 2006/0189548 A1 | 8/2006 | Himmelsbach et al. |
| 2006/0217323 A1 | 9/2006 | Patel et al. |
| 2006/0229260 A1 | 10/2006 | Rybczynski et al. |
| 2006/0234954 A1 | 10/2006 | Urbanski |
| 2006/0247179 A1 | 11/2006 | Fushimi et al. |
| 2006/0258749 A1 | 11/2006 | Eckhardt et al. |
| 2006/0293251 A1 | 12/2006 | Urbanski et al. |
| 2007/0027092 A1 | 2/2007 | Himmelsbach et al. |
| 2007/0049537 A1 | 3/2007 | Eckhardt et al. |
| 2007/0060531 A1 | 3/2007 | Kikuchi et al. |
| 2007/0060545 A1 | 3/2007 | Nomura et al. |
| 2008/0027122 A1 | 1/2008 | Nomura et al. |
| 2008/0119422 A1 | 5/2008 | Nomura et al. |
| 2008/0132563 A1 | 6/2008 | Kakinuma et al. |
| 2008/0146515 A1 | 6/2008 | Nomura et al. |
| 2008/0234366 A1 | 9/2008 | Bindra et al. |
| 2009/0124702 A1 | 5/2009 | Siva Satya Krishna Babu et al. |
| 2009/0233874 A1 | 9/2009 | Abdel-Magid et al. |
| 2010/0099883 A1 | 4/2010 | Fillers et al. |
| 2011/0009347 A1 | 1/2011 | Liang et al. |
| 2011/0087017 A1 | 4/2011 | Farina et al. |
| 2011/0212905 A1 | 9/2011 | Nomura et al. |
| 2012/0058941 A1 | 3/2012 | Nomura et al. |
| 2012/0115799 A1 | 5/2012 | Wang et al. |

FOREIGN PATENT DOCUMENTS

| | | | |
|---|---|---|---|
| EP | 0348184 | B1 | 3/1993 |
| EP | 0579204 | A2 | 1/1994 |
| EP | 0579204 | A3 | 1/1994 |
| EP | 0625513 | B1 | 9/1999 |
| EP | 1172362 | A1 | 1/2002 |
| EP | 1338603 | A1 | 8/2003 |
| EP | 1528066 | A1 | 5/2005 |
| EP | 1845095 | | 10/2007 |
| EP | 1956023 | A1 | 3/2008 |
| GB | 2359554 | | 8/2001 |
| JP | 59039889 | A | 3/1984 |
| JP | 63-233975 | A | 9/1988 |
| JP | 4-253974 | A | 9/1992 |
| JP | 06246354 | A | 9/1994 |
| JP | 07242526 | A | 9/1995 |
| JP | 9-263549 | A | 10/1997 |
| JP | 2000-34230 | A | 2/2000 |
| JP | 2000-34239 | A | 2/2000 |
| JP | 2001-288178 | A | 10/2001 |
| JP | 2002167430 | A | 6/2002 |
| JP | 2003-12686 | A1 | 1/2003 |
| JP | 2003238417 | A | 8/2003 |
| JP | 2003313168 | A | 11/2003 |
| WO | 93/09100 | A1 | 5/1993 |
| WO | 93/21178 | A1 | 10/1993 |
| WO | 94/14807 | A1 | 7/1994 |
| WO | 97/17949 | A1 | 5/1997 |
| WO | 97/25033 | A1 | 7/1997 |
| WO | 98/42347 | A1 | 10/1998 |
| WO | WO 99/67236 | A | 12/1999 |
| WO | 00/27823 | A1 | 5/2000 |
| WO | 00/28989 | A1 | 5/2000 |
| WO | 00/74681 | A1 | 12/2000 |
| WO | 01/27128 | | 4/2001 |
| WO | 01/32157 | A1 | 5/2001 |
| WO | 01/64669 | A1 | 9/2001 |
| WO | 01/68660 | A1 | 9/2001 |
| WO | 01/74834 | A1 | 10/2001 |
| WO | 01/74835 | A1 | 10/2001 |
| WO | 01/85167 | A1 | 11/2001 |
| WO | 02/26706 | A2 | 4/2002 |
| WO | 02/053573 | A1 | 7/2002 |
| WO | 02/068439 | A1 | 9/2002 |
| WO | 02/068440 | A1 | 9/2002 |
| WO | 02/070020 | A2 | 9/2002 |
| WO | 02/070020 | A3 | 9/2002 |
| WO | 02/083066 | A2 | 10/2002 |
| WO | 02/088157 | A1 | 11/2002 |
| WO | 02/094262 | A1 | 11/2002 |
| WO | 02/096357 | A2 | 12/2002 |
| WO | 03/000712 | A1 | 1/2003 |
| WO | 03/011880 | A1 | 2/2003 |
| WO | 03/020737 | A1 | 3/2003 |
| WO | 03/043621 | A1 | 5/2003 |
| WO | 03/087104 | A1 | 10/2003 |
| WO | 03/099836 | A1 | 12/2003 |
| WO | 2004/007517 | A1 | 1/2004 |
| WO | 2004/013118 | A1 | 2/2004 |
| WO | 2004/014931 | A1 | 2/2004 |
| WO | 2004/019958 | A1 | 3/2004 |
| WO | 2004/052902 | A1 | 6/2004 |
| WO | 2004/052903 | A1 | 6/2004 |
| WO | 2004/063209 | A2 | 7/2004 |
| WO | 2004/063209 | A3 | 7/2004 |
| WO | WO 2004/064806 | A | 8/2004 |
| WO | 2004/076470 | A2 | 9/2004 |
| WO | 2004/080990 | A1 | 9/2004 |
| WO | 2004/087727 | A1 | 10/2004 |
| WO | 2004/099230 | A1 | 11/2004 |
| WO | 2004/113359 | A1 | 12/2004 |
| WO | 2005/009539 | A2 | 2/2005 |
| WO | 2005/009954 | A2 | 2/2005 |
| WO | 2005/012326 | A1 | 2/2005 |
| WO | 2005/058845 | A2 | 6/2005 |
| WO | 2006/010557 | | 2/2006 |
| WO | 2006/080577 | A1 | 8/2006 |
| WO | 2006/108842 | A1 | 10/2006 |
| WO | 2007/025943 | A2 | 3/2007 |
| WO | 2007/031548 | A2 | 3/2007 |
| WO | 2007/087441 | A2 | 8/2007 |
| WO | 2008/013322 | A1 | 1/2008 |
| WO | 2008/020011 | A2 | 2/2008 |
| WO | 2008/034859 | A1 | 3/2008 |
| WO | 2008/055870 | A1 | 5/2008 |
| WO | 2008/055940 | A2 | 5/2008 |
| WO | 2008/070609 | A1 | 6/2008 |
| WO | WO 2008/069327 | A | 6/2008 |
| WO | WO 2008069327 | A1 * | 6/2008 |
| WO | 2009/022010 | A1 | 2/2009 |
| WO | 2009/023537 | | 2/2009 |
| WO | 2009/026537 | A1 | 2/2009 |
| WO | 2009/035969 | A1 | 3/2009 |
| WO | 2009/091082 | A1 | 7/2009 |
| WO | 2009/121945 | A2 | 10/2009 |

OTHER PUBLICATIONS

Albertoni Borghese et al., "Inhibitors of sodium/glucose cotransport.", Drugs of The Future, Apr. 2009, pp. 297-305, vol. 34(4), Prous Science, XP007915342.

(56) References Cited

OTHER PUBLICATIONS

Amishiro et al., "Synthesis and Antitumor Activity of Duocarmycin Derivatives: A-Ring Pyrrole Compounds Bearing 5-Membered Heteroarylacryloyl Groups," Chem. Pharm. Bull., Oct. 1999, pp. 1393-1403, vol. 47(10).
Appleton et al., "A Mild and Selective C-3 Reductive Alkylation of Indoles", Tetrahedron Letters, 1993, pp. 1529-1532, vol. 34(9).
Apsel et al., "General Entries to C-aryl glycosides. Formal synthesis of galtamycinone.", Tetrahedron Letters, 2003, pp. 1075-1077, vol. 44.
Arakawa et al., "Improved diabetic syndrome in C57BL/KsJ-db/db Mice by Oral Administration of the Na+-Glucose Cotransporter Inhibitor T-1095." *British Journal of Pharmacology*, 2001, pp. 578-586, vol. 132.
Banker, Modern Pharmaceutics, Third Edition, Marcel Dekker, Inc., published 1996, p. 596.
Beck-Nielsen et al., "In Vivo Glucose Metabolism, Insulin Secretion and, Insulin Action in Europids with non-insulin-dependent Diabetes mellitus (NIDDM) and Their First-degree Relatives.", Diabetic Medicine, Sep. 1996, pp. S78-S84, vol. 13(9 Supp. 6).
Benhaddou et al.,"Tetra-n-propylammonium tetra-oxoruthenate(VII): a reagent of choice for the oxidation of diversely protected glycopyranoses and glycofuranoses to lactones", Carbohydrate Research, 1994, pp. 243-250, vol. 260.
Bertolini et al., "A New Simple One-Pot Regioselective Preparation of Mixed Diesters of Carbonic Acid.", Journal of Organic Chemistry, 1998, pp. 6031-6034, vol. 63(17).
Blair et al., "Effect of Ring Fluorination on the Pharmacology of Hallucinogenic Tryptamines", J. Med. Chem., 2000, pp. 4701-4710, vol. 43.
Boehm et al., "Novel Inhibitors of DNA Gyrase: 3D Structure Based Biased Needle Screening, Hit Validation by Biophysical Methods, and 3D Guided Optimization. A Promising Alternative to Random Screening," J. Med. Chem., 2000, pp. 2664-2674, vol. 43(14).
Bookser, B.C., "2-Benzyloxymethy1-5-(tributylstannyptetrazole. A reagent for the preparation of 5-aryl-and 5-heteroaryl-1 H-tetrazoles via the Stille reaction," Tetrahedron Letters, 2000, pp. 2805-2809, vol. 41.
Bouillon et al., "Synthesis of novel halopyridinylboronic acids and esters. Part 2: 2,4, or 5-Halopyridin-3-yl-boronic acids and esters," Tetrahedron, 2002, pp. 3323-3328, vol. 58.
Bouillon et al., "Synthesis of novel halopyridinylboronic acids and esters. Part 3: 2, or 3-Halopyridin-4-yl-boronic acids and esters," Tetrahedron, 2002, pp. 4369-4373, vol. 58.
Bouillon et al., "Synthesis of novel halopyridinylboronic acids and esters. Part 4: Halopyridin2-yl-boronic acids and esters are stable, crystalline partners for classical Suzuki cross-coupling," Tetrahedron, 2003, pp. 10043-10049, vol. 59.
Braga et al., "Making crystals from crystals: a green route to crystal engineering and polymorphism.", Chem. Commun., 2005, pp. 3635-3645.
Brooks et al., "Boron Trichloride/Tetra-n-Butylammonium Iodide: A Mild, Selective Combination Reagent for the Cleavage of Primary Alkyl Aryl Ethers", J. Org. Chem., 1999, pp. 9719-9721, vol. 64.
CAS Reg. No. 487001-40-1, IPOrganisers, Entered STN Feb. 7, 2003, pp. 1-2.
Caumo et al., "Insulin Sensitivity from Meal Tolerance Tests in Normal Subjects: A Minimal Model Index.", J. of Clinical Endocrinology & Metabolism, 2000, pp. 4396-4402, vol. 85(11).
Cicchillo et al., "A convenient synthesis of glycosyl chlorides from sugar hemiacetals using triphosgene as the chlorine source," Carbohydrate Research, 2000, pp. 431-434, vol. 328.
Clayden et al., "Dearomatizing Cyclization of Arylsulfonylalkoxymethyl Lithiums: A Route to the Podophyllotoxin Skeleton," Organic Letters, 2003, pp. 831-834, vol. 5(6).
Comins et al., "Synthesis of 3-Substituted Indoles Via N-Acylindolium Ions", Tetrahedron Letters, 1986, pp. 1869-1872, vol. 27(17).

Cottet et al., "Recommendable Routes to Trifluoromethyl-Substituted Pyridine—and Quinolinecarboxylic Acids," Eur. J. Org. Chem., 2003, pp. 1559-1568.
Czernecki et al., "C-Glycosides. 7. Stereospecific C-Glycosylation of Aromatic and Heterocyclic Rings", J. Org. Chem., 1989, pp. 610-612, vol. 54.
De Las Heras et al., "Alkylating Nucleosides 1. Synthesis and Cytostatic Activity of N-Glycosyl(halomethyl)-1,2,3-triazoles. A New Type of Alkylating Agent," Journal of Medicinal Chemistry, 1979, pp. 496-501, vol. 22(5).
Deeg et al., "Pioglitazone and Rosiglitazone Have Different Effects on Serum Lipoprotein Particle Concentrations and Sizes in Patients With Type 2 Diabetes and Dyslipidemia.", Diabetes Care, Oct. 2007, pp. 2458-2464, vol. 30(10).
Deetjen et al., "Renal Handling of D-Glucose and Other Sugars", Textbook of Nephrology, 3rd Edition, 1995, pp. 90-94. vol. 1.
Devivar et al., "Benzimidazole Ribonucleosides: Design, Synthesis, and Antiviral Activity of Certain 2-(Alkylthio)- and 2-(Benzylthio)-5,6-dichloro-1-(β-D-ribofuranosyl)benzimidazolesl.", J.Med. Chem., 1994, pp. 2942-2949, vol. 37.
Dewynter et al., "Synthesis of Pseudomucleosides containing Chiral Sulfahydantoins as Aglycone (II)", Tetrahedron, 1996, pp. 993-1004, vol. 52(3).
Dillard et al., "Indole Inhibitors of Human Nonpancreatic Secretory Phospholipase A2. 1. Indole-3-acetamides", J. Med. Chem., 1996, pp. 5119-5136, vol. 39.
Dinneen, S.F., "The Postprandial State: Mechanisms of Glucose Intolerance.", Diabetic Medicine, Aug. 1997, pp. S19-S24, vol. 14, Issue S3.
Dondoni et al., "Stereoselective synthesis of C-glycosylphosphonates from their ketols. Reconsideration of an abandoned route", Tetrahedron: Asymmetry, 2000, pp. 305-317, vol. 11.
Dondoni et al., "Thiazole-Based Synthesis of Formyl C-Glycosides", J. Org. Chem., 1994, pp. 6404-6412, vol. 59.
Dudash et al., "Glycosylated dihydrochalcones as potent and selective sodium glucose co-transporter 2 (SGLT2) inhibitors," Bioorganic & Medicinal Chemistry Letters, 2004, pp. 5121-2125, vol. 14.
Dunn et al., "Analgetic and antiinflammatory 7-Aroylbenzofuran-5-ylacetic acids and 7-Aroylbenzothiophene-5-ylacetic Acids.", Journal of Med. Chem., 1986, pp. 2326-2329, vol. 29(1).
Eid et al., "Reaction of Some 1,2,4-Triazines with Acetobromoglucose", Arch. Pharm (Weinheim), 1990, pp. 243-245, vol. 323.
Ellsworth et al., "Aglycone exploration of C-arylglucoside inhibitors of renal sodium-dependent glucose transporter SGLT2," Bioorganic & Medicinal Chemistry Letters, 2008, pp. 4770-4773, vol. 18.
Ellsworth et al., "C-Arylglucoside synthesis: triisopropylsilane as a selective reagent for the reduction of an anomeric C-phenyl ketal," Tetrahedron: Asymmetry, 2003, pp. 3243-3247, vol. 14.
Emancipator, K., "Laboratory diagnosis and monitoring of diabetes mellitus.", Am J Clin Pathol., Nov. 1999, pp. 65-674, vol. 112(5).
Frahn et al., "Functionalized AB-Type Monomers for Suzuki Polycondensation," Synthesis, Nov. 1997, pp. 1301-1304.
Fresneda et al., "Synthesis of the indole alkaloids meridianins from the tunicate *Aplidium meridianum*" Tetrahedron, 2001, pp. 2355-2363, vol. 57.
Fuller et al., "Thienothiophenes. Part 2. Synthesis, metallation and bromine-lithium exchange reactions of thieno[3,2-b-thiophene and its polybromo derivatives," J. Chem. Soc., Perkin Trans. 1., 1997, pp. 3465-3470.
Ganesh et al., "Synthesis and biological evaluation of fluorescently labeled epothilone analogs for tubulin binding studies," Tetrahedron, 2003, pp. 9979-9984, vol. 59.
Gershell, L., "Type 2 diabetes marker", Nature Reviews Drug Discovery, May 2005, pp. 367-368, vol. 4.
Gohier et al., "ortho-Metalation of Unprotected 3-Bromo and 3-Chlorobenzoic Acids with Hindered Lithium Dialkylamides", J. Org. Chem., 2003, pp. 2030-2033, vol. 68.
Goldberg R.B., "Prevention of Type 2 Diabetes.", Medical Clinics of North America, Jul. 1998, pp. 805-821, vol. 82(4).

(56) References Cited

OTHER PUBLICATIONS

Gong, H., et al., "Diasteroselective Ni-Catalyzed negishi Cross Coupling Approach to Saturated, Fully Oxygenated C-Alkyl and C-Aryl Glycosides.", Journal of the American Chemical Society, Sep. 10, 2008, pp. 12177-12183, vol. 130(36), XP002612364.

Goodman & Gilman's the Pharmacological Basis of Therapeutics, 10th Edition, McGraw-Hill Medical Publishing Division, 2001, pp. 54-57.

Greene et al., "Protective Groups in Organic Synthesis.", 3rd Edition, 1999, pp. 116-121.

Greene et al., "Protective Groups in Organic Synthesis.", 3rd Edition, 1999, pp. 170.

Gronowitz et al., "Some Substitution Reactions of 1-(2-Thienyl)pyrazole and 1-(3'- Thienyl)pyrazole," Chemica Scripta., 1979, pp. 157-161, vol. 13.

Groop et al., "Characterization of the Prediabetic State.", American Journal of Hypertension, Sep. 1997, pp. 172S-180S, vol. 10(9Part2).

Gros et al., "Efficient and Regioselective Access to Bis-heterocycles via Palladium-Catalysed Coupling of Organostannanes and Organozincates Derived from C—6 Lithiated 2-Methoxypyridine," Synthesis, 1999, pp. 754-756, No. 5.

Haffner S.M., "Impaired Glucose Tolerance, Insulin Resistance and Cardiovascular Disease.", Diabetic Medicine, Aug. 1997, pp. S12-S18, vol. 14.

Haffner S.M., "The Prediabetic Problem: Development of Non-Insulin-Dependent Diabetes Mellitus and Related Abnormalities.", Journal of Diabetes and Its Complications, Mar.-Apr. 1997, pp. 69-76, vol. 11(2).

Han et al., "Dapagliflozin, a Selective SGLT2 Inhibitor, Improves Glucose Homeostasis in Normal and Diabetic Rats", Diabetes, Jun. 2008, pp. 1723-1729, vol. 57, New York.

Handlon, A. L., "Sodium glucose co-transporter 2 (SGLT2) inhibitors as potential antidiabetic agents," Expert Opin. Ther. Patents, 2005, pp. 1531-1540, vol. 15(11).

Hixon et al., "Sizing Materials by Crushing and Grinding.", Chemical Engineer, Nov. 1990, pp. 94-103.

Hofslokken et al., "Convenient Method for the ortho-Formylation of Phenols.", Acta Chemica Scandinavica, 1999, pp. 258-262, vol. 53.

Hongu et al., "Na+-Glucose Cotransporter Inhibitors as Antidiabetic Agents. II.[1]) Synthesis and Structure—Activity Relationships of 4'-Dehydroxyphlorizin Derivatives.", Chem. Pharm. Bull., 1998, pp. 22-33, vol. 46(1).

Horton et al., "Synthetic Routes to Higher-Carbon Sugars. Reaction of Lactones with 2-Lithio-1,3-Dithiane", Carbohydrate Research, 1981, pp. 27-41, vol. 94.

Hu et al., "A New Approach Towards the Yellowing Inhibition of Mechanical Pulps. Part I: Selective Removal of alpha-Hydroxyl and alpha-Carbonyl Groups in Lignin Model Compounds", Holzforschung, 1999, pp. 43-48, vol. 53(1).

Huang-Minlon, "Reduction of Steroid Ketones and other Carbonyl Compounds by Modified Wolff-Kishner Method", J. Am. Chem. Soc., Oct. 1949, pp. 3301-3303, vol. 71.

Ibrahim et al., "Facile Approach for the Selective Glycodisation of Cyclic Asymmetric Amides and Thioamides", Carbohydrate Letters, 1996, pp. 425-432, vol. 1.

Ibrahim et al., "Selective Synthesis and Structure of 2-N- and 3-S-Glucosyl-1,2,4-Triazoles of Potential Biological Interest", Carbohydrate Letters, 1999, pp. 331-338, vol. 3(5).

Idris et al., "Sodium-glucose co-transporter-2 inhibitors: an emerging new class of oral antidiabetic drug.", Diabetes, Obesity and Metabolism, 2009, pp. 79-88, vol. 11(2), GB, XP007915350.

Isaji, M., "Sodium-glucose cotransporter inhibitor for diabetes," Current Opinion in Investigational Drugs, 2007, pp. 285-292, vol. 8(4).

Jain et al., "Polymorphism in Pharmacy.", Indian Drugs, 1986, pp. 315-329, vol. 23(6).

Kaelin et al., "General Strategies for the Synthesis of the Major Classes of C-aryl Glycosides.", J. Am. Chem. Soc., 2001, pp. 6937-6938, vol. 123.

Kahn et al., "Normalization of Blood Glucose in Diabetic Rats with Phlorizin Treatment Reverses Insulin-resistant Glucose Transport in Adipose Cells without Restoring Glucose Transporter Gene Expression.", Journal of Clinical Investigation, 1991, pp. 561-570, vol. 87.

Kanai et al., "The Human Kidney Low Affinity Na+/Glucose Cotransporter SGLT2: Delineation of the Major Renal Reabsorptive Mechanism for D-Glucose", J. Clin. Invest., Jan. 1994, pp. 397-404, vol. 93.

Kasahara et al., "A missense mutation in the Na+/glucose cotransporter gene SGLT1 in a patient with congenital glucose-galactose malabsorption: normal trafficking but inactivation of the mutant protein," Biochimica et Biophysics Acta, 2001, pp. 141-147, vol. 1536.

Katz et al., "Quantitative Insulin Sensitivity Check Index: A Simple, Accurate Method for Assessing Insulin Sensitivity in Humans.", J. Of Clin. Endocrinology & Metabolism, 2000, pp. 2040-2410, vol. 85(7).

Ketcha et al., "Synthesis of Alyl-Substituted N-Protected Indoles via Acylation and Reductive Deoxygenation1" J. Org. Chem., 1989, pp. 4350-4356, vol. 54.

Khan et al, "Reactions of Phenyl-Substituted Heterocyclic Compounds—II. Nitrations and Brominations of 1-Phenylpyrazole Derivatives," Canadian Journal of Chemistry, 1963, pp. 1540-1547, vol. 41.

Kitagawa, K., et al., "Halogen—Magnesium Exchange via Trialkylmagnesates for the Preparation of Aryl- and Alkenylmagnesium Reagents", Angew. Chem. Int. Ed., 2000, pp. 2481-2493, vol. 39(14).

Klapars et al., "Copper-Catalyzed Halogen Exchange in Aryl Halides: An Aromatic Finkelstein Reaction", J. Am. Chem. Soc., 2002, pp. 14844-14845, vol. 124(50).

Knochel, P., et al., Organic Reactions, vol. 58, Chapter 2: Preparation and Application of Functionalized Organozinc Compounds by., pp. 417-490, Edited by L. E. Overman, et al., John Wiley &Sons, Inc., Publishers.

Lee et al., "Recent Advances in Aryl C-Glycoside Synthesis.", Current Topics in Medicinal Chemistry, 2005, pp. 1333-1350, vol. 5.

Lee et al., "Synthesis and in Vitro Activity of Novel Isoxazolyl Tetrahydropyridinyl Oxazolidinone Antibacterial Agents," Bioorganic & Medicinal Chemistry Letters, 2003, pp. 4117-4120, vol. 13.

Lieberman et al., "Pharmaceutical Dosage Forms.", Second Edition, 1990, Marcel Dekker Inc., pp. 462-472, vol. 2.

Lin et al., "Syntheses of Guanidinoglycosides with the Inventive use of Mitsunobu Conditions and 1, 8-Diazabicyclo[5.4.0]undec-7-ene.", Synthesis, 2003, pp. 255-261, No. 2.

Link et al., "A method for preparing C-glycosides related to phlorizin" Tetrahedron Letters, 2000, pp. 9213-9217, vol. 41.

Lipscombe et al., "Trends in diabetes prevalence, incidence, and mortality in Ontario, Canada 1995-2005: a population-based study", Lancet, 2007, vol. 369, pp. 750-756.

Maatooq et al., "C-p-Hydroxybenzoylglycoflavones From Citrullus Colocynthis.", Phytochemistry, Jan. 1997, pp. 187-190, vol. 44(1).

Mackenzie et al., "Biophysical Characteristics of the Pig Kidney Na+/Glucose Cotransporter SGLT2 Reveal a Common Mechanism for SGLT1 and SGLT2", J. Biol. Chem., 1996, vol. 271, pp. 32678-32683, No. 5.

Manis et al., "Metabolism of 4,4'-Methylenebis(2-chloroaniline) by Canine Liver and Kidney Slices.", Drug Metabolism and Disposition, 1986, pp. 166-174, vol. 14(2).

Marsenic, O. Md, "Glucose Control by the Kidney: An Emerging Target in Diabetes.", Am. J. of Kidney Diseases, May 2009, pp. 875-883, vol. 53(5).

Martin, S. F., "Unified Strategy for the Synthesis of C-aryl glycosides*.", Pure Appl. Chem., 2003, pp. 63-70, vol. 75(1).

Matsuda et al., "Insulin Sensitivity Indices Obtained From Oral Glucose Tolerance Testing: Comparison with the euglycemic insulin clamp," Diabetes Care, Sep. 1999, pp. 1462-1470, vol. 22(9).

Matthews et al., "Homeostasis model assessment: insulin resistance and—cell function from fasting plasma glucose and insulin concentrations in man," Diabetolgia, 1985, pp. 412-419, vol. 28.

Meanwell et al., "Regiospecific Functionalization of 1,3-Dihydro-2H-benzimidazol-2-one and Structurally Related Cyclic Urea Derivates.", J. Org. Chemistry, 1995, pp. 1565-1582, vol. 60(6).

(56) References Cited

OTHER PUBLICATIONS

Meng et al., "Discovery of Dapagliflozin: a Potent, Selective Renal Sodium-Dependent Glucose Cotransporter 2 (SGLT2) Inhibitor for the Treatment of Type 2 Diabetes", J. Med. Chem., 2008, pp. 1145-1149, vol. 51(5).
Messaoudi et al, "Synthesis and biological evaluation of oxindoles and benzimidazolinones derivatives," European Journal of Medicinal Chemistry, 2004, pp. 453-458, vol. 39.
Mewshaw et al., "New Generation Dopaminergic Agents. 7. Heterocyclic Bioisosteres that Exploit the 3-Oh-Phenoxyethylamine D2 Template", Bioorganic & Medicinal Chemistry Letters, 1999, pp. 2593-2598, vol. 9.
Miyaura et al., "Palladium-Catalyzed Cross-Coupling Reactions of Organoboron Compounds.", Chem. Rev., 1995, pp. 2457-2583, vol. 95(7).
Mongin, F., et al., "Deprotonation of furans using lithium magnesates", Tetrahedron Lett., 2005, pp. 7989-7992, vol. 46.
Nishimura et al, "Tissue-specific mRNA Expression Profiles of Human ATP-binding Cassette and Solute Carrier Transporter Superfamilies," Drug Metab. Pharmacokinet., 2005, pp. 452-477, vol. 20(6).
Nomura et al., "Discovery of canagliflozin, a novel C-glucoside with thiophene ring, as sodium dependent glucose cotransporter 2 inhibitor for the treatment of type 2 diabetes mellitus.", Journal of Med. Chem., Sep. 9, 2012, pp. 6355-6360, vol. 53(17), American Chemical Society, US, XP007915324.
Nomura, S., "Renal Sodium-Dependent Glucose Cotransporter 2 (SGLT2) Inhibitors for New Anti-Diabetic Agent," Current Topics in Medicinal Chemistry, 2010, pp. 411-418, vol. 10(4).
Ohsumi et al. "Pyrazole-O-Glucosides as Novel Na+-Glucose Cotransporter (SGLT) Inhibitors" Bioorganic & Medicinal Chemistry Letters, 2003, pp. 2269-2272, vol. 13.
Oku et al., "T-1095, an Inhibitor of Renal Na+-Glucose Cotransporters, May Provide a Novel Approach to Treating Diabetes", Diabetes, Sep. 1999, pp. 1794-1800, vol. 48.
Orjales et al. "New 2-Piperazinylbenzimidazole Derivatives as 5-HT-3 Antagonists. Synthesis and Pharmacological Evaluation," J. Med. Chem., 1997, pp. 586-593, vol. 40.
Parker et al., "Reductive Aromatization of Quinols: Synthesis of the C-Arylglycoside Nucleus the Paulacandins and Chaetiacandin," Organic Letters, 2000, pp. 497-499, vol. 2(4).
Parrott, E.L., "Milling of pharmaceutical solids.", Journal of Pharmaceutical Sciences, Jun. 1974, pp. 813-829, vol. 63(6).
Patani et al., "Bioisosterism: A Rational Approach in Drug Design", Chem. Rev., American Chemical Society, 1996, pp. 3147-3176, vol. 96.
Peng et al., "Post-transcriptional Regulaton of Na+/Glucose Cotransporter (SGTL1) Gene Expression in LLC-PK1 Cells.", Journal of Biological Chemistry, 1995, pp. 20536-20542, vol. 270(35).
Perry's Chemical Engineers Handbook, Sixth Edition, 1984, pp. 21-13 to 21-19.
Pharmaceutical Sciences, Remington, 17th Ed., pp. 1585-1594 (1985).
Polshettiwar et al., "Pd-N-heterocycle carbene (NHR) organic silica: synthesis and application in carbon-carbon coupling reactions.", Tetrahedron, May 12, 2008, pp. 4637-4643, vol. 64(20), Elsevier Science Publishers, Amsterdam, NL, XP022607642.
Ramlo-Halsted B.A. & Edelman S.V., "The Natural History of Type 2 Diabetes Mellitus: Implications for Clinical Practice.", Primary Care, Dec. 1999, pp. 771-789, vol. 26(4).
Raynaud et al., "Revised Concept for the Estimation of Insulin Sensitivity From a Single Sample.", Diabetes Care, Jun. 1999, pp. 1003-1004, vol. 22(6).
Rosenstock et al., "Canagliflozin, an Inhibitor of Sodium Glucose Co-Transporter 2 (SGLT2), Improves Glycemic Control and Lowers Body Weight in Subjects with Type 2 Diabetes (T2D) on Metformin.", Diabetes, Jun. 1, 2010, pp. A21, vol. 59(supp. 1), American Diabetes Association, US, XP009139979.
Rosetti et al., "Correction of Hyperglycemia with Phlorizin Normalizes Tissue Sensitivity to Insulin in diabetic rats.", Journal of Clinical Investigation, 1987, pp. 1510-1515, vol. 79.
Rosetti et al., "Effect of Chronic Hyperglycemia on In Vivo Insulin Secretion in Partially Pancreatectomized Rats.", Journal of Clinical Investigation, 1987, pp. 1037-1044, vol. 80.
Rosetti et al., "Glucose Toxicity."; Diabetes Care, 1990, pp. 610-630, vol. 13.
Schultheiss et al., "Pharmaceutical Cocrystals and Their Physicochemical Properties.", Crystal Growth and Design, Jun. 3, 2009, pp. 2950-2967, vol. 9(6), XP55011939.
Shan et al., "The role of cocrystals in pharmaceutical science.", Drug Discovery Today, May 1, 2008, pp. 440-446, vol. 13(9-10), Elsevier, Rahway, NJ, US, XP022649919.
Silverman, R. B., "The Organic Chemistry of Drug Design and Drug Action," Academic Press, 1992, pp. 19-23.
Somei et al., "The First and Simple Total Synthesis of Cappariloside Al," Heterocycles, 2000, pp. 1573-1578, vol. 53(7).
Srogl et al., "Sulfonium salts. Participants par excellence in metal-catalyzed carbon-carbon bond-forming reactions.", Journal of the American Chemical Society, Jan. 1, 1997, pp. 12376-12377, vol. 119, American Chemical Society, US, XP002955770.
Stoner et al., "Benzylation via Tandem Grignard Reaction—Lodotrimethylsilane (TMSI) Mediated.Reduction," Tetrahedron, 1995, pp. 11043-11062, vol. 51(41).
Stumvoll et al., "Use of the Oral Glucose Tolerance Test to Assess Insulin Release and Insulin Sensitivity.", Diabetes Care, Mar. 2000, pp. 295-301, vol. 23(3).
Tanaka et al. "Solid-Phase Synthesis of—Mono-Substituted Ketones and an Application to the Synthesis of a Library of Phlorizin Derivatives", Synlett, 2002, pp. 1427-1430, No. 9.
Thornber, C.T., "Isosterism and Molecular Modification in Drug Design.", Chem. Society Review, 1979, pp. 563-580, vol. 8.
Tilak et al, "Carcinogenesis by Thiophene Isosters of Polycyclic Hydrocarbons," Tetrahedron, 1960, pp. 76-95, vol. 9.
Tsujihara et al., "Na+ Glucose Cotransporter (SGLT) Inhibitors as Antidiabetic Agents. 4. Synthesis and Pharmacological Properties of 4'-Dehydroxyphlorizin Derivatives Substituted on the B Ring.", Journal of Medicinal Chemistry, 1999, pp. 5311-5324, vol. 42.
Tsujihara et al., Bio Clinica, 1998, pp. 324-328, vol. 13(4), English language Abstract.
Turk et al., "Glucose/galactose malabsorption caused by a defect in the Na+/glucose cotransporter," Nature, Mar. 1991, pp. 354-356, vol. 350.
Ueta et al., "Long-term treatment with the Na+-glucose contransporter inhibitor T1095 causes sustained improvement in hyperglycemia and prevents diabetic neuropathy in Goto-Kakizaki Rats.", Life Sci., 2005, pp. 2655-2668, vol. 76(23).
Unger et al., "Hyperglycemia as an inducer as well as a consequence of impaired islet cell function and insulin resistance: implications for the management of diabetes.", Diabetologia, 1985, pp. 119-21, vol. 28.
Vippagunta et al., "Crystalline Solids". Advanced Drug Delivery Reviews, 2001, pp. 3-26, vol. 48.
Vishweshwar et al., "Pharmaceutical co-crystals.", Journal of Pharmaceutical Sciences, Mar. 1, 2006, pp. 499-516, vol. 95(3), American Pharmaceutical Association, Washington, US.
Wallace et al., "Use and Abuse of Homa Modeling.", Diabetes Care, Jun. 2004, pp. 1487-1495, vol. 27(6).
Wang et al, "Selective monolithiation of 2,5-dibromopyridine with butyllithium," Tetrahedron Letters, 2000, pp. 4335-4338, vol. 41.
Wareham et al., "Is There Really an epidemic of diabetes?", Diabetologia, 2005, pp. 1454-1455, vol. 48.
Washburn, W. N., "Evolution of sodium glucose co-transporter 2 inhibitors as anti-diabetic agents," Expert Opin. Ther. Patents, 2009, pp. 1485-1499, vol. 19(11).
Watanabe et al., "Cyclopentyl Methyl Ether as a New and Alternative Process Solvent.", Organic Process Research and Development, 2007, pp. 251-258, vol. 11.
Wild et al., "Global Prevalence of Diabetes: Estimates for the year 2000 and projections for 2030," Diabetes Care, May 2004, pp. 1047-1053, vol. 27(5).

(56) References Cited

OTHER PUBLICATIONS

Wolff, M. E., vol. 1: Principles and Practice, Burger's Medicinal Chemistry and Drug Discovery, 5th Edition, 1995, pp. 975-977.

Wright, E.M., "Renal Na+-glucose cotransporters," Am J Physiol Renal Physiol, 2001, pp. F10-F18, vol. 280.

Wurster D.E., "Air-suspension Technique of Coating Drug Particles* A Preliminary Report.", Journal of the American Pharmaceutical Association, Aug. 1959, pp. 451-454, vol. 48(8).

Wurster, D.E., "Preparation of compressed tablet granulations by the air-suspension technique II.", Journal of the American Pharmaceutical Association, 1960, pp. 82-84, vol. 49(2).

Yang et al., "Convergent C-Glycolipid Synthesis via the Ramberg-Backlund Reaction: Active Antiproliferative Glycolipids", Org. Lett. 1999, pp. 2149-2151, vol. 1913).

Yoshimura et al., "Discovery of Novel and PotenCRetinoic Acid Receptor alpha-- Agonists: Synthesis and Evaluation of Benzofuranyl-pyrrole and Benzothiophenyl-pyrrole Derivatives," J. Med. Chem., 2000, pp. 2929-2937, vol. 43.

Zamani et al., "Synthesis and Structure Determination of Some New N-Glycosides of 4,5-Disubstituted-1,2,4-triazole-3-thiones.", Journal of the Chinese Chemical Society, 2002, pp. 1041-1044, vol. 49.

Zhdanov, Y. et al., "Application of organozinc compounds in the synthesis of carboncarbon derivatives of sugars.", Database CA (online), Chemical Abstracts Service, Columbus, Ohio, USA, XP002612365.

Translation--Zhdanov, Y. et al., "Application of organozinc compounds in the synthesis of carbon-carbon derivatives of sugars.", Database CA (online), Chemical Abstracts Service, Columbus, Ohio, USA, XP002612365.

Zhou, F. Y., "The Synthesis and Characterization of 1-Benzyl-3-N-(Beta-D-glucosie-1-yl)-4-fluorouracil", Hecheng Huaxue, 2001, pp. 272-274, vol. 9(3).

Schmidt et al., "Synthese von Pyrazol-, Pyrazolo[3,4-d]pyrimidin- und 1H-1,2,4-Triazolgluconucleosiden aus Glucosehydrazonen," Liebigs Ann. Chem., 1981, pp. 2309-2317.

* cited by examiner

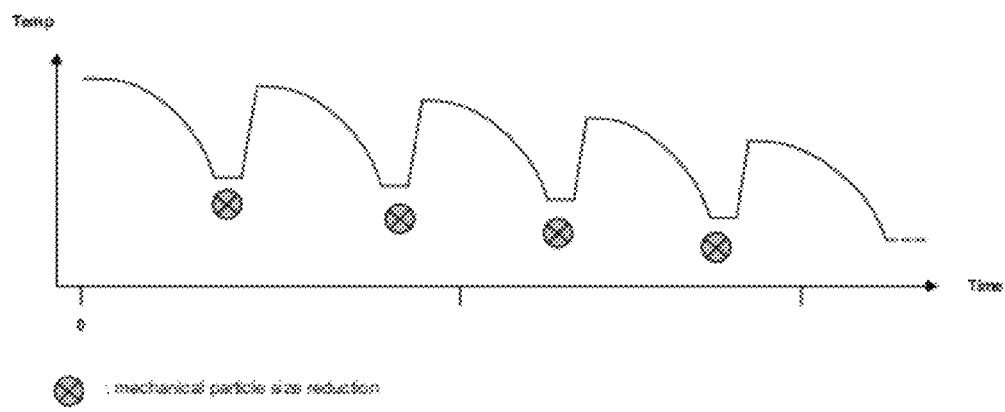
Figure 1: graphical presentation of four temperature oscillation episodes and four mechanical particle size reduction episodes

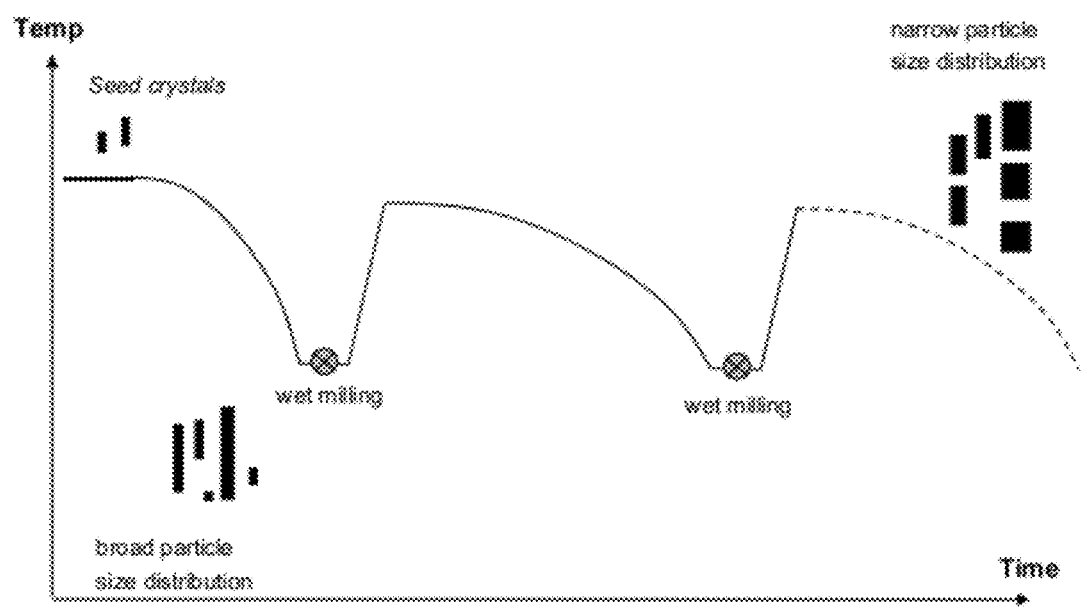
Figure 2 : graphical presentation of temperature oscillation and wet milling

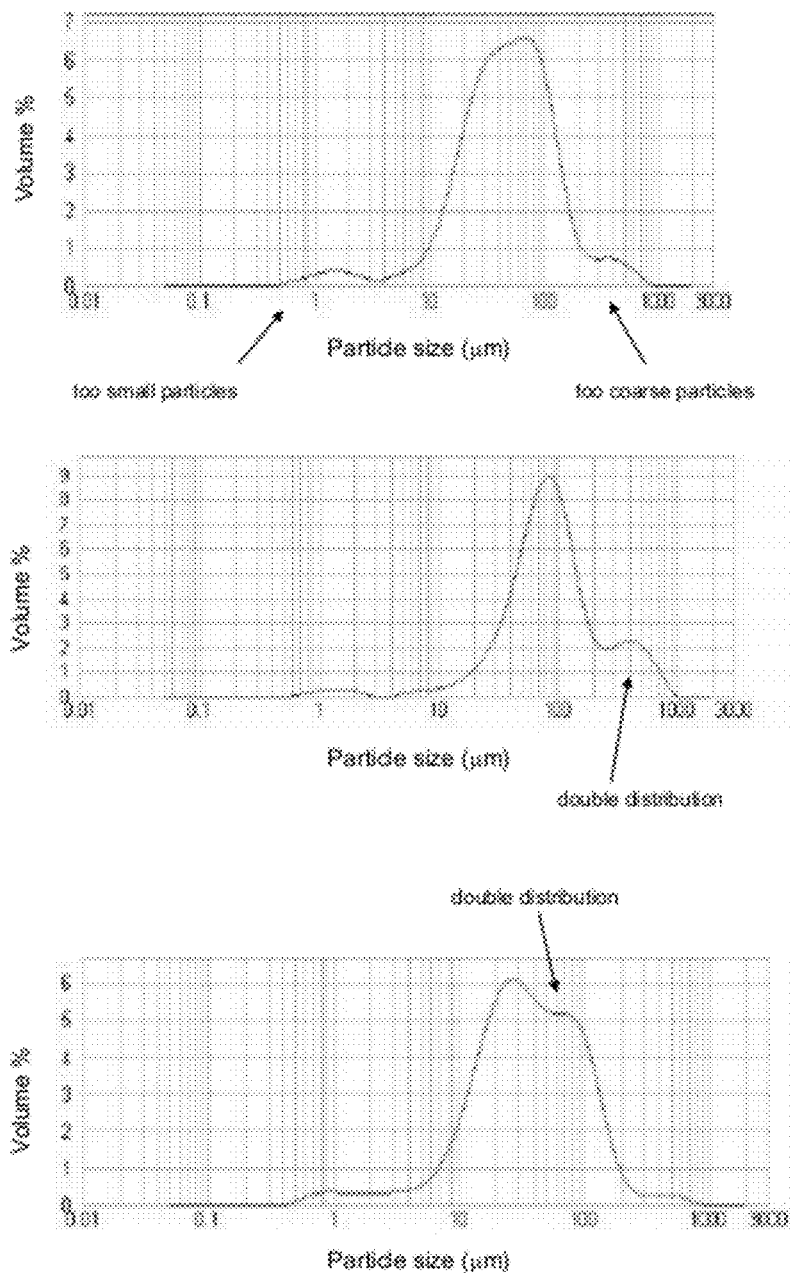
Figure 3 : particle size distribution of compound (I) obtained by classical cooling crystallisation or anti-solvent crystallisation Figure 4 : particle size distribution of compound (I) obtained using temperature oscillation and wet milling with a high shear machine as described in Example 1
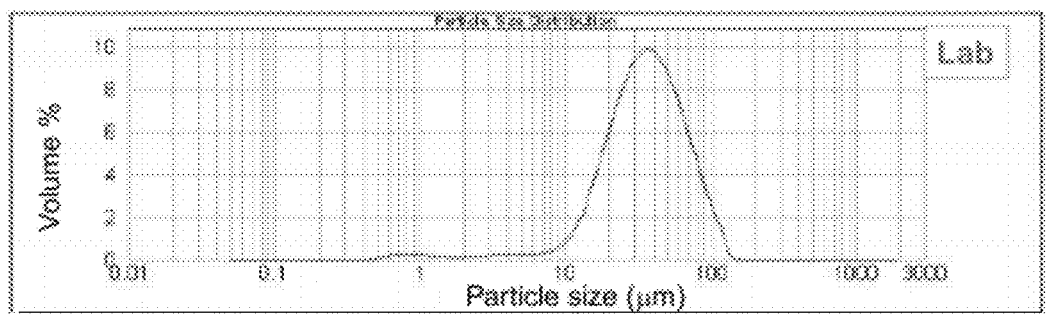
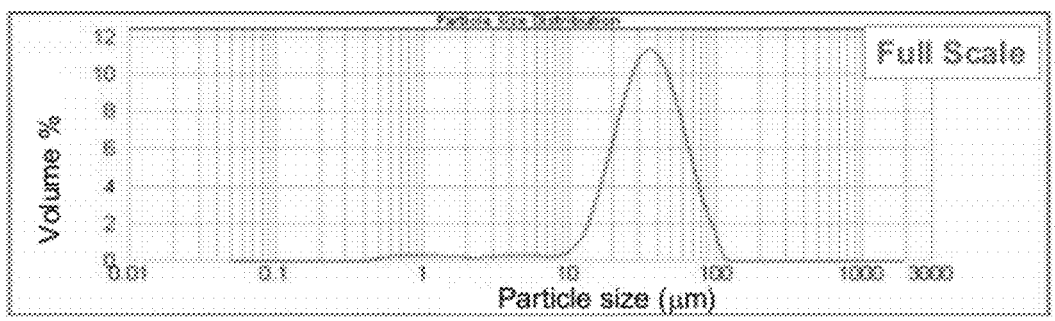

CRYSTALLISATION PROCESS FOR 1-(β-D-GLUCOPYRANOSYL)-4-METHYL-3-[5-(4-FLUOROPHENYL)-2-THIENYLMETHYL] BENZENE

CROSS REFERENCE TO RELATED APPLICATIONS

This application is the U.S. national stage of Application No. PCT/EP2010/059817, filed Jul. 8, 2010, which application claims priority from EP 09165125.7, filed Jul. 10, 2009.

The present invention relates to a crystallisation procedure to obtain 1-(β-3-D-glucopyranosyl)-4-methyl-3-[5-(4-fluorophenyl)-2-thienylmethyl] benzene hemi-hydrate crystals having a narrow particle size distribution and improved flowability, bulk and tap density properties.

The compound 1-(β-D-glucopyranosyl)-4-methyl-3-[5-(4-fluorophenyl)-2-thienylmethyl] benzene is a inhibitor of sodium-dependent glucose transporter (SGLT) and thus of therapeutic use for the treatment of diabetes, obesity, diabetic complications, and the like. It is described in WO-2005/012326 as compound (84) having the following structure:

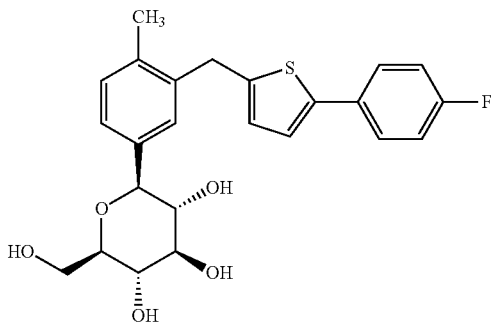 [SMILES: Cc1ccc([C@@H]2O[C@H](CO)[C@@H](O)[C@H](O)[C@H]2O)cc1Cc1ccc(-c2ccc(F)cc2)s1]

A crystalline form of this compound is disclosed in WO-2008/069327.

In general, for commercial use it is important that Active Pharmaceutical Ingredients (API's) should have good handling qualities. Additionally, there is a need to produce the API in a pure and crystalline form to enable formulations to meet specific pharmaceutical requirements.

Crystal engineering is of importance in the production of API's. During crystallisation, many physico-chemical characteristics of the API or drug substance are defined, including crystal polymorph, shape, size, particle size distribution, chemical purity and stability. These characteristics influence the stirrability, residual solvent level, drying time, agglomeration, fragmentation and attrition during the isolation process, which in turn affects the drug product manufacturing by determining particle flow, compressibility, solubility, dissolution rate and bioavailability. The specifications towards the physical properties of the API, driven by the drug product manufacturing, are very narrow concerning particle size distribution, bulk density, electrostatic charge and flowability.

It has been observed that the crystalline 1-(β-D-glucopyranosyl)-4-methyl-3-[5-(4-fluorophenyl)-2-thienylmethyl] benzene hemihydrate (referenced to as "compound (I)" throughout the patent description), prepared using the classic cooling or anti-solvent crystallisation techniques has a large particle size distribution with a lot of fine particles and coarse particles which negatively impacts the drug product manufacturing. Examples of such a particle size distribution of compound (I) are given in FIG. 3.

It has now been found that crystalline 1-(β-D-glucopyranosyl)-4-methyl-3-[5-(4-fluoro-phenyl)-2-thienylmethyl] benzene hemihydrate (i.e. compound (I)) can be obtained with a narrow particle size distribution when the crystallisation process comprises at least one temperature oscillation episode and at least one mechanical particle size reduction episode. It has been found that the crystalline compound (I) so obtained has a narrow particle size distribution and improved flowability, bulk and tap density properties.

FIG. 1 is a graphical presentation of a crystallisation process according to the present invention comprising of four temperature oscillation episodes and four mechanical particle size reduction episodes.

Crystallisation procedures using temperature oscillation and/or mechanical particle size reduction have been disclosed in WO-99/67236 and WO-2004/064806.

The temperature oscillation episode, also called Ostwald ripening, is performed by heating and cooling the suspension comprising crystalline compound (I) to a predetermined temperature, conveniently under stirring. The following parameters for the temperature oscillation episode can be controlled:

the start temperature before heating
the heating time, the rate of heating and temperature/time profile
the maximum temperature and the duration thereof (temperature holding step)
the cooling time, rate of cooling and temperature/time profile
the end temperature after cooling Said temperature oscillation parameters depend upon the nature of the solvent or solvent mixture, the nature of the crystals, the desired particle size and particle size distribution and may be optimized using standard tests.

The temperature amplitude, i.e. the difference between the starting temperature and the maximum temperature of the temperature oscillation episode, may be chosen to bring a significant amount of compound (I) into solution, e.g. between 10 and 60%. The amplitude may range according to the desired solubility difference between 5° C. and 20° C. The amplitude may be the same or different for each temperature oscillation episode.

The temperature oscillation curve may be in the form of approximately a sinus curve with a temperature holding step or approximately a zig-zag curve, i.e. a curve comprising a linear heating step and a linear cooling step. Alternatively, the cooling step may also use a cubic cooling profile.

In order to avoid a total process time of several days, the heating time and cooling time in the temperature oscillation episode may be each e.g. about 10 minutes to 120 minutes. Between heating and cooling, there may be a temperature holding step, e.g. a duration of about 5 to 10 minutes. Preferably, the heating time may be shorter than the cooling time, e.g. a heating time of about 10 to 15 minutes and a cooling time of about 60 to 120 minutes.

In general, the higher the number of temperature oscillation episodes the narrower the particle size distribution becomes. In practice, the number of episodes may be about 1 to 6.

Each temperature oscillation episode is alternated with a mechanical particle size reduction episode. The mechanical particle size reduction of the crystals of compound (I) in suspension may be done by milling or micronisation using ultrasound.

Mechanical particle size reduction by ultrasound may be performed by subjecting the crystalline suspension to a sonication energy whose frequency is above that which is detectable by the human ear: i.e. higher than 16 kHz to 20 kHz. Ultrasonic treatment may be used either batchwise or semi-continuously, either in an ultrasonic bath or in a vessel fitted with a submersible ultrasonic generator, or as a continuous flow process using either an ultrasonic bath as the generator or a flow-through ultrasonic cell. The duration of the ultrasonic treatment, and the frequency and intensity of the radiation can be selected by those skilled in the art to achieve the desired end result. The mechanical particle size reduction process by ultrasound can be followed by particle size analysis of samples periodically removed from the system.

Mechanical particle size reduction of the compound (I) crystals in suspension can also be performed by wet milling or wet grinding using a shearing machine such as a high-speed rotor-stator device or high shear mill. Wet milling can be carried out either by placing the shearing machine in the reactor containing the suspension of compound (I) crystals, or by passing said crystalline suspension continuously into the shearing machine. Suitable shearing machines are e.g. of the Turrax® type, magic LAB®, or Dispax-Reactor® type, sold by IKA®-Werke GmbH & Co. KG in Germany. These high shear milling machines can use different types of milling disks such as "2G, 4M and 6F generators" depending upon the desired particle size and/or milling time. Some of these machines are suitable for treating industrial amounts ranging up to the point of allowing a flow rate of 100 m$^3$/hour.

Mechanical particle size reduction using wet milling is preferred for the treatment of industrial amounts of Active Pharmaceutical Ingredients (API's). Particle size reduction by ultrasound presents problems when large volumes have to be treated since the efficacy of the ultrasound emitter decreases beyond a few centimeters from said emitter. Also high-power ultrasound can cause premature wear of the metals and welds of the apparatus used since ultrasound causes cavitation close to the walls of the ultrasound emitter possibly leading to metal leaching. Said metal leaching may contaminate the API.

Particle size analysis of the compound (I) crystals in suspension during the crystallisation process can be done with a Lasentec focused-beam reflectance measurement (FBRM) system.

In an embodiment the present invention relates to a process for preparing crystalline compound (I) comprising the consecutive steps of
a) preparing a solution of compound (I) in a solvent system under concentration and temperature conditions which allow the total solubility of compound (I);
b) cooling the said solution to a temperature such that the solution in the metastable zone;
c) seeding the solution of compound (I) with crystals of compound (I);
d) cooling the solution of compound (I) to obtain a suspension of crystals of compound (I);
e) subjecting the crystalline suspension thus formed to mechanical particle size reduction using a shearing machine;
f) heating the crystalline suspension of compound (I) to dissolve the fine particles;
g) repeat steps d), e) and f) from 1 to 6 times;
h) cooling the crystalline suspension of compound (I) to room temperature or lower;
i) filtering off the crystals of compound (I) thus formed.

The solvent, solvent mixture or solvent system used in the crystallisation process of the present invention can be any organic solvent, or mixture of organic solvents, wherein there is a large difference in solubility of compound (I) between the lowest and the highest temperature of the temperature oscillation episode. The solvent or solvent mixture may contain water up to 20% which may result in a two phase solvent mixture.

In practice it has been found that ester type solvents such as, e.g. ethyl aceate, or 1-methylethyl aceate, are suitable for the crystallisation procedure of the present invention. These ester type solvents may optionally comprise water.

The conditions for the crystallisation procedure of the present invention are dependent upon the solvent system used. For instance when the solvent system is a mixture of 1-methylethyl acetate and water wherein water is present in an amount from 0.1% to 1.8% v/v, then the following conditions apply:
step b): the temperature ranges between 52° C. and 56° C., in particular about 54° C.,
step c): seeding with microfine crystals of compound (I) in an amount of about 0.5%
step d): cooling is in accordance with a cubic temperature profile to a temperature between 36° C. and 40° C., in particular about 38° C.
step e): wet milling using a high shear machine
step f): the suspension of crystalline compound (I) is heated to a temperature between 52° C. and 56° C., in particular about 55° C.;
step h): the crystalline suspension of compound (I) is cooled a room temperature or lower, in particular to 0° C.

For 1-(β-D-glucopyranosyl)-4-methyl-3-[5-(4-fluorophenyl)-2-thienylmethyl] benzene hemihydrate (i.e. compound (I)) it has been found that the desired narrow particle size distribution can be obtained using a first temperature oscillation episode, followed by a first mechanical particle size reduction episode, a second temperature oscillation episode, a second mechanical particle size reduction episode, and a third temperature oscillation episode. Thereafter, the suspension is cooled in order to reduce the solubility of the crystals of compound (I) in the solvent and the crystals are then isolated by filtration and dried. The particle size distribution of compound (I) obtained using this procedure is demonstrated in FIG. 4 and shows a narrow particle size distribution without the presence of a double distribution and fine or coarse particles as for crystalline compound (I) obtained using the classic cooling or anti-solvent crystallisation techniques (see FIG. 3).

Example 1

A solution of 1-(β-D-glucopyranosyl)-4-methyl-3-[5-(4-fluorophenyl)-2-thienylmethyl] benzene hemihydrate (i.e. compound (I)) (317.5 g) in 1-methylethyl acetate (1400 ml) and water (15.6 ml) was heated till 72.5° C. until a clear solution was obtained and filtered. The filter was rinsed with 1-methyl-ethyl acetate (175 ml) and the reaction mixture was allowed to cool to a temperature of 54° C. The reaction mixture was seeded with compound (I) (1.59 g) and the mixture was stirred for 2 hours.

The reaction mixture was cooled according to a cubic temperature decrease described below:
to 52.4° C. over 20 minutes
to 49.0° C. over 20 minutes
to 44.4° C. over 20 minutes
to 38° C. over 20 minutes The crystalline suspension was subjected to wet milling using a high shear mill for 25 minutes (Dispax-Reactor® type DR 2000/20 from IKA®-Werke GmbH & Co. KG in Germany with a 2P or 4M milling disk.

The reaction mixture was then heated to a temperature of 55° C. and subsequently cooled according to a cubic temperature decrease described below:
- to 54.0° C. over 25 minutes
- to 52.4° C. over 25 minutes
- to 47.1° C. over 25 minutes
- to 38° C. over 25 minutes The crystalline suspension was subjected to wet milling using a high shear mill for 25 minutes using the same conditions as set out above.

The reaction mixture was then heated to a temperature of 55° C. and subsequently cooled according to a cubic temperature decrease described below:
- to 54.0° C. over 25 minutes
- to 52.4° C. over 25 minutes
- to 41.4° C. over 30 minutes
- to 0° C. over 105 minutes The suspension was stirred for 4 hours at a temperature of 0° C. The precipitate was filtered off and washed with 1-methylethyl acetate (175 ml) and dried under vacuum.

Example 2

Particle size of original compound (I) and crystallised compound (I) according to the procedure of Example 1 have been determined with laser diffraction (LD). For this purpose, a Malvern Mastersizer 2000 laser diffractometer (Malvern, U.K.) has been used, which was equipped with a Hydro 2000S wet dispersion module. Prior to analysis, an amount of ca. 200 mg of the product was dispersed in 1% (w/v) polysorbate 20 in water by means of vigorous shaking for 30 seconds. A representative portion of this dispersion was than added to the reservoir of the wet dispersion module, which for this purpose was filled with water. The liquid medium was circulated via the measurement cell of the instrument, to allow measurement of the product specific scattering pattern. Based on the scattering intensities as measured under different angles relative to the incoming collimated laser beam, for compound (I) the particle size distribution (PSD) by volume was calculated based on the Fraunhofer optical model. For the PSD, the d10, d50 and d90 cumulative undersize were reported as the relevant statistical descriptors.

TABLE 1 particle size distribution

|  | D10 | D50 | D90 |
| --- | --- | --- | --- |
| original compound (I) | 14 μm | 43 μm | 116 μm |
| crystallised compound (I) | 20 μm | 49 μm | 102 μm |

As can be seen from Table 1, the compound (I) crystals prepared according to the present invention have a narrow and well defined particle size distribution with less fine and coarse percentiles (see the improved D10 and D90 values).

The graphical representation of the particle size distribution of compound (I) obtained by classical cooling or anti-solvent crystallisation can be found in FIG. 3. The particle size distribution of compound (I) obtained using temperature oscillation and wet milling with a high shear machine as described in Example 1 can be found in FIG. 4. As can be seen by comparing these series of graphical particle size distribution figures, the particle size distribution of crystalline compound (I) obtained using temperature oscillation and wet milling with a high shear machine does not show the presence of a double distribution and is absent of fine or coarse particles.

Example 3

The bulk and tap densities of the crystallised 1-(β-D-glucopyranosyl)-4-methyl-3-[5-(4-fluorophenyl)-2-thienylmethyl] benzene hemihydrate were measured. The bulk density of 25 g of compound (I) was measured by recording its volume in a 100-ml graduated cylinder. Tap density volume was then measured after 500 taps.

TABLE 2 bulk and tap density

|  | Bulk density (g/ml) | Tap density (g/ml) |
| --- | --- | --- |
| original compound (I) | 0.28 | 0.48 |
| crystallised compound (I) | 0.35 | 0.54 |

In general a higher bulk density and a smaller difference between tap and bulk densities gives better powder flow and manufacturability.

The bulk density for the crystallised compound (I) according to Example 1 is 20% higher than for original compound (I).

DESCRIPTION OF THE DRAWINGS

FIG. 1: graphical presentation of four temperature oscillation episodes and four mechanical particle size reduction episodes FIG. 2: graphical presentation of temperature oscillation and wet milling FIG. 3: particle size distribution of compound (I) obtained by classical cooling or anti-solvent crystallisation FIG. 4: particle size distribution of compound (I) obtained using temperature oscillation and wet milling with a high shear machine as described in Example 1

The invention claimed is:

1. A process for preparing 1-(β-D-glucopyranosyl)-4-methyl-3-[5-(4-fluorophenyl)-2-thienylmethyl] benzene hemihydrate crystals comprising
    subjecting a crystalline suspension of 1-(β-D-glucopyranosyl)-4-methyl-3-[5-(4-fluorophenyl)-2-thienylmethyl] benzene hemihydrate in a solvent system to at least one temperature oscillation episode and at least one mechanical particle size reduction episode.

2. The process according to claim 1 wherein the temperature oscillation episode comprises a heating phase and a corresponding cooling phase.

3. The process according to claim 2 wherein the heating phase precedes the cooling phase.

4. The process according to claim 3 wherein the mechanical particle size reduction is performed by wet milling.

5. The process according to claim 4 wherein the temperature oscillation episode precedes the mechanical particle size reduction episode.

6. The process according to claim 4 wherein the temperature oscillation episode and the mechanical particle size reduction episode are repeated independently from one another.

7. The process according to claim 1 wherein the solvent system is an organic solvent, or mixture of organic solvents, wherein 1-(β-D-gluco-pyranosyl)-4-methyl-3-[5-(4-fluorophenyl)-2-thienylmethyl] benzene hemihydrate has a large difference in solubility between the lowest and the highest temperature of the temperature oscillation episode.

8. The process according to claim 1 wherein the solvent system is selected from ethyl acetate, 1-methylethyl acetate, or a mixture thereof, and said solvent system optionally comprises up to 20% water.

9. The process of claim 1 comprising the consecutive steps of
- a) preparing a solution of compound (I) in a solvent system under concentration and temperature conditions which allow the total solubility of compound (I);
- b) cooling the said solution to a temperature such that the solution is in the metastable zone;
- c) seeding the solution of compound (I) with crystals of compound (I);
- d) cooling the solution of compound (I) to obtain a suspension of crystals of compound (I);
- e) subjecting the crystalline suspension thus formed to mechanical particle size reduction using a shearing machine;
- f) heating the crystalline suspension of compound (I) to dissolve the fine particles;
- g) repeat steps d), e) and f) from 1 to 5 times;
- h) cooling the crystalline suspension of compound (I) to room temperature or lower;
- i) filtering off the crystals of compound (I) thus formed.

10. The process according to claim 9 wherein the solvent system in step a) is a mixture of 1-methylethyl acetate and water.

11. The process according to claim 10 wherein the temperature in step b) is 54° C.

12. The process according to claim 11 wherein cooling of the solution of compound (I) in step d) is in accordance with a cubic temperature decrease.

13. The process according to claim 12 wherein the crystalline suspension of compound (I) in step f) is heated to 55° C.

14. The process according to claim 13 wherein step d), e) and f) are repeated 1 time.

15. The process according to claim 14 wherein the crystalline suspension of compound (I) in step h) is cooled to 0° C.

* * * * *